United States Patent
Cheppa et al.

(10) Patent No.: US 9,308,286 B2
(45) Date of Patent: Apr. 12, 2016

(54) HEATING APPARATUS WITH A DISINFECTION DEVICE

(71) Applicant: DENTSPLY International Inc., York, PA (US)

(72) Inventors: Edward Cheppa, Pittsburgh, PA (US); Kevin Wilkinson, Bixby, OK (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 14/137,639

(22) Filed: Dec. 20, 2013

(65) Prior Publication Data

US 2014/0178248 A1    Jun. 26, 2014

Related U.S. Application Data

(60) Provisional application No. 61/740,618, filed on Dec. 21, 2012.

(51) Int. Cl.
| | | |
|---|---|---|
| *A61L 2/26* | (2006.01) | |
| *A61L 2/10* | (2006.01) | |
| *A61L 2/04* | (2006.01) | |

(52) U.S. Cl.
CPC ... *A61L 2/26* (2013.01); *A61L 2/04* (2013.01); *A61L 2/10* (2013.01); *A61L 2202/121* (2013.01); *A61L 2202/122* (2013.01); *A61L 2202/21* (2013.01); *A61L 2202/24* (2013.01)

(58) Field of Classification Search
CPC .............. A61L 2/10; A61L 2/08; A61L 2/04; A61L 2/26
See application file for complete search history.

(56) References Cited

U.S. PATENT DOCUMENTS

| | | | |
|---|---|---|---|
| 4,515,651 A * | 5/1985 | MacLaughlin | B29C 65/0618 156/379.8 |
| 7,202,484 B1 | 4/2007 | Tantillo | |
| 2002/0146343 A1 | 10/2002 | Jenkins et al. | |
| 2003/0034459 A1 | 2/2003 | Bonin | |
| 2005/0194026 A1 | 9/2005 | Lu | |
| 2007/0148764 A1* | 6/2007 | Suzuki et al. | 435/293.1 |
| 2009/0169426 A9 | 7/2009 | Toepfer et al. | |
| 2010/0108917 A1* | 5/2010 | Stanley et al. | 250/504 R |
| 2010/0111590 A1* | 5/2010 | Pires | A45D 33/02 401/195 |

(Continued)

FOREIGN PATENT DOCUMENTS

| | | |
|---|---|---|
| EP | 2160203 A1 | 3/2010 |
| WO | 9314668 A1 | 8/1993 |

(Continued)

OTHER PUBLICATIONS

PCT/US2013/077274 PCT International Search Report.
PCT/US2013/077274 PCT Written Opinion.

*Primary Examiner* — Regina M Yoo
(74) *Attorney, Agent, or Firm* — David A. Zdurne; Douglas J. Hura; Leana Levin

(57) ABSTRACT

A heating apparatus for heating and sterilizing or disinfecting a material used in dental treatment, the heating apparatus comprising a heating compartment with a heating element for heating all or part of the material within the heating compartment; at least one holder for receiving and holding at least a part of the material used in dental treatment inside the heating compartment; and an disinfection device having a light source for sterilizing all or part of the material within the heating compartment.

8 Claims, 4 Drawing Sheets

(56) References Cited

U.S. PATENT DOCUMENTS

2010/0150775 A1* 6/2010 Reddy et al. .................. 422/28
2013/0230821 A1   9/2013 Brown
2014/0060094 A1* 3/2014 Shur et al. .................... 62/129

FOREIGN PATENT DOCUMENTS

| WO | 9806351 A1 | 2/1998 |
| WO | 2013030279 A1 | 3/2013 |

* cited by examiner

HEATING APPARATUS WITH A DISINFECTION DEVICE

RELATED APPLICATIONS

This patent application claims the benefit of and priority to U.S. Provisional Patent Application Ser. No. 61/740,618, filed on Dec. 21, 2012, which is herein incorporated by reference for all purposes.

FIELD OF INVENTION

The present invention relates to a disinfection device. More particularly, an embodiment of the present invention relates to a disinfection device that can emit light, such as ultraviolet light, for a predetermined period of time to disinfect one or more tools and/or products that may be used by a dentist, orthodontist, endodontist, or other dental personnel. In other embodiments, the disinfection device may clean or disinfect other tools such as tools used by surgeons, doctors, nurses, or other medical personnel.

BACKGROUND OF THE INVENTION

Ultraviolet light has a wavelength that is shorter than visible light, but is longer than X-rays. Ultraviolet light is typically considered to be light having a wavelength within the range of 10 nanometers to 400 nanometers. Ultraviolet light can help different substances glow or fluoresce and may also provide non-ionizing radiation.

Dental tools such as a dental explorer, a periodontal probe, a straight probe, a mouth prop, a dental mirror, a cheek retractor, a tongue retractor, a lip retractor, curette, a scaler, a tartar scraper, a scraper, a burnisher, an elevator, a dental forcep, a ligature, a distal end cuter, a file, an endodontic explorer, or a dental bur are commonly used during dental medical checkups or procedures such as a teeth cleaning, a root canal, a removal of one or more teeth, or other dental or orthodontic procedures.

Cleaning such tools can often take a fairly long period of time. The long period of time needed to clean or disinfect the tools can require delays in providing service to customers or require dentists or orthodontists to have a relatively large inventory of tools due to the fact that numerous tools are unclean after providing a service to one patient and need to be replaced with other tools while the dirty tools are cleaned.

It is believed that a new tool or device is needed that can permit quick and effective disinfection of one or more dental tools such as tools used by a dentist, dental hygienist, or orthodontist. Examples of such tools include rotary and hand endodontic files, reamers, paper points and Gutta Percha points. It would be preferred for such a tool or device to be configured so that tools could be quickly disinfected so that bacteria will not be introduced into a human body (e.g part of the mouth, part of a tooth canal, etc.) during a subsequent use of that tool. Such a delay would preferably be between 5 seconds and two minutes, such as a delay of 10, 20 or 30 seconds or one minute. The metallurgical properties of the tools may not be damaged by such disinfection.

It is further contemplated that dental products such as endodontic obturators, paper points, and Gutta Perch points could be disinfected with this invention. Incorporating the ultraviolet light within an obturator oven allows the molten Gutta Percha to be disinfected just prior to insertion of the obturator in the patient's root canal.

SUMMARY OF THE INVENTION

In one aspect, the present invention is directed to heating apparatus for heating and sterilizing or disinfecting a material used in dental treatment, the heating apparatus comprising a heating compartment with a heating element for heating all or part of the material within the heating compartment; at least one holder for receiving and holding at least a part of the material used in dental treatment inside the heating compartment; and an disinfection device having a light source for sterilizing all or part of the material within the heating compartment.

In another aspect, the present invention contemplates a method for heating and sterilizing or disinfecting a material used in dental treatment, comprising the steps of inserting at least a portion of the material through an opening and into a cavity of a heating compartment that includes a heating element and an ultraviolet light source; applying heat to the at least a portion of the material, with an intensity sufficient to soften the at least a portion of the material while juxtaposed to the heating element; and applying ultraviolet light to the at least a portion of the material, with an intensity sufficient to sterilize or disinfect the at least a portion of the material while juxtaposed to the ultraviolet light source.

In yet another aspect, any of the aspects of the present invention may be further characterized by one or any combination of the following features: the light source emits ultra violet light; the holder is an actuating member; the actuating member includes at least a first position and a second position such that in the first position the heating element, the light source, or both are turned off and in the second position, the heating element, the light source, or both are turned on; the actuating member includes an actuator, triggered by the detection the actuating member being in the second position, to enable both the heat to be output from the heating element and light to be output from the light source; a greater portion of the dental material is positioned within the heating compartment in the second position relative to the first position; further comprising a light seal to block light output from the light source from exiting the heating compartment, wherein the material and/or the actuating member forms part of the compartment seal; the material and/or the actuating member forms part of the compartment seal when the actuating member is in the second position; the heating compartment is disposed within a housing, the heating compartment including an internal cavity that extends therein to an opening, which extends through a top surface of the housing; the heat output and the light output may be pulsed at the same time or at different time; further comprising the step of actuating movement of an actuating member, wherein the actuating member is moved from a first position in which the heating element, the light source, or both are turned off to a second position in which the heating element, the light source, or both are turned on; the actuating movement step, at least a partial compartment seal is formed about the opening of the heating compartment using at least part of the material and/or the actuating member; the actuating member is moved from the first position in which the heating element and the light source are both turned off to the second position in which the heating element and the light source are both turned on

BRIEF DESCRIPTION OF THE DRAWINGS

Present preferred disinfection devices are shown in the accompanying drawings and certain present preferred methods of practicing or making the same are also illustrated therein. It should be understood that like reference numbers used in the drawings may identify like components.

DETAILED DESCRIPTION OF EXEMPLARY EMBODIMENTS

Figure 1:
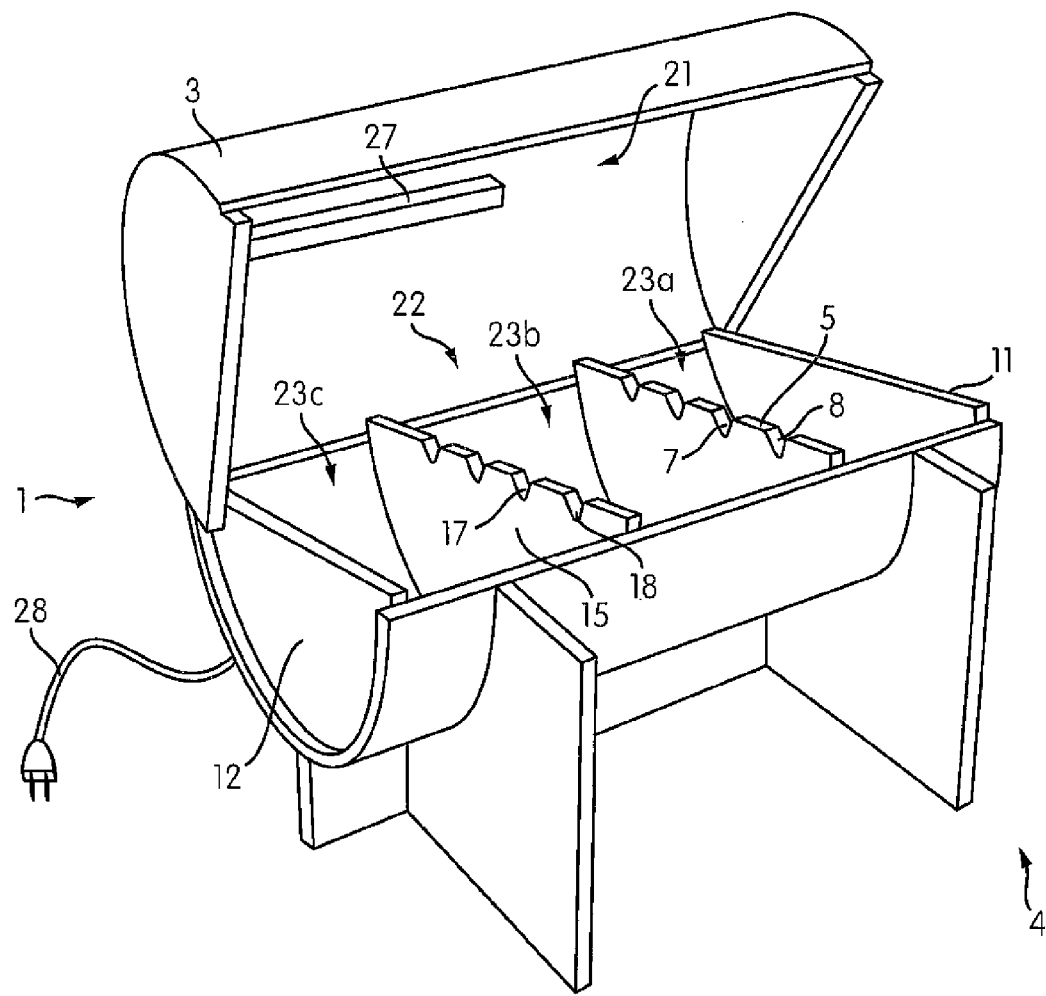
FIG. 1 is a perspective view of a first exemplary embodiment of the present invention which may include a device with a lid in an open position.

A disinfection device is provided that includes a base and a moveable lid that is attached to the base. The base defines at least one cavity therein for retaining or receiving one or more dental tools. A light that may emit ultraviolet light is attached to the base or the lid. When the lid is closed, the light emits ultraviolet light at a predetermined wattage level for a predetermined period of time to disinfect the tools stored in the at least one cavity of the device.

The obturator oven embodiment includes an ultraviolet light mounted on the heater block within the oven. The heater block may include one or more openings to permit ultraviolet light to enter the cavity containing the obturator. The heater block may contain a plurality of walls for mounting heating elements and/or ultraviolet lights.

In some embodiments, the base of the device that has the at least one cavity may include a plurality of walls that are positioned within a central cavity of the base. The top edges of the walls may include apertures such as grooves, openings, or gaps that are sized to receive different portions of different dental tools. The walls may be spaced apart from each other such that a first aperture in one of the walls is aligned with a first aperture formed in the other walls so that a tool may be positioned so that it extends horizontally and transverse to the height of the walls so that the tool is supported by the different spaced apart walls and held in its position via the first apertures of the walls.

In other embodiments, the base of the device may include different sidewalls that each has a recess or other aperture formed therein that is sized to receive a portion of respective ends of a dental tool. Each side wall or end wall may have multiple spaced apart apertures aligned with an aperture on an opposite sidewall. A tool may be held in position within the cavity of the base of the device by having opposite ends of the tool positioned in the apertures of the opposing sidewalls. In yet other embodiments, the base may include one or more projections or holders that are located within the cavity of the base to maintain a tool positioned therein at a particular position or orientation.

The base and lid of the disinfection device may also include a reflective liner. The reflective liner may be positioned on the walls of the device as well in some embodiments. The liner or multiple liners can be used to provide one or more reflective liners that cover the entire inner surface of the lid, base and walls. The reflective liner can reflect the ultraviolet light emitted by the light so that the emitted ultraviolet light is exposed to the entire tool or substantially the entire tool positioned in the device.

In another embodiment of my device, the device may be configured to also, or alternatively, hold and disinfect tools used by medical doctors or surgeons. The tools held within the cavity of the device may include a dental tool, a medical tool, or an orthodontic tool. Examples of orthodontic tools or dental tools are a dental explorer, a periodontal probe, a straight probe, a mouth prop, a dental mirror, a cheek retractor, a tongue retractor, a lip retractor, curette, a scaler, a tartar scraper, a scraper, a burnisher, an elevator, a dental forceps, a ligature, a distal end cutter, a file, an endodontic explorer, or a dental bur.

A method of using my device is also provided. The method includes placing one or more tools within an embodiment of my disinfection device, closing the lid of the device a first time, actuating the light of my device to emit ultraviolet light within the cavity of the device for a predetermined period of time, opening the lid of my device for a first time, and removing the one or more tools positioned therein.

In other embodiments of my method, the tools are repositioned after the lid is opened. The lid is then again closed a second time. The light is again actuated to emit the ultraviolet light for the predetermined period of time and the lid of the device is then opened a second time. The tools are then removed after the lid is opened the second time. The repositioning of the tools may be used to ensure that the emitted light is exposed to the entire surface area of a tool. Depending on how the base of the device is constructed, light may not be exposed to the entire surface area of a tool until the tool is repositioned so that the tool is at least exposed to the ultraviolet light for a predetermined period of time while in two different orientations. Depending on the shape of the tool, it is possible that a third or fourth iteration of the repositioning of the tool and opening and closing of the lid and actuating of the light could also be needed.

Referring to FIG. 1, a disinfection device may include a moveable lid 3 that is moveable attached to a base 4 so that the lid 3 is moveable from an open position to a closed position. For instance, the lid 3 may be hingedly connected to the base or may be otherwise moveably attached to the base 4 so that the lid is moveable from an open position to a closed position.

The base 4 of the device defines a cavity 22 and the lid is shaped to have a cavity 21 as well. When the lid 3 is in the closed position, a large cavity is defined within the device, which is the merged cavities of the base and lid 22 and 21, which are in communication with each other when the lid 3 is in the closed position.

The base 4 may include multiple feet or supports to support the base 4 on a surface, such as a desktop, tabletop, a floor, or other work surface. The base 4 also include a first end wall 11 and a second end wall 12 opposite the first end wall 11. A first wall 5 and a second wall 15 are also attached to the base. The first and second walls 5 and 15 are located within the cavity 22 of the base. The first and second walls may define subparts to the cavity 22. For instance, the first wall 5 and the first end wall 11 may define a first opening 23a within the cavity 22 of the base. The first and second walls 5 and 15 may define a second opening 23b and the second wall 15 and the second end wall 12 may define a third opening 23c. The first wall may include a plurality of horizontally spaced openings or apertures such as a first aperture 7 and a second aperture 8 formed on the top edge of the first wall 5. The second wall 15 may also include horizontally spaced apart apertures such as a first aperture 17 and a second aperture 18. The first aperture 7 of the first wall 5 may be aligned with the first aperture 17 of the second wall so that a tool may be positioned in the first apertures 7 and 17 so that the tool may extend horizontally from the first aperture 17 of the second wall 15 to the first aperture 7 of the first wall 5.

The second aperture 8 of the of the first wall 5 may be aligned with the second aperture 18 of the second wall so that a tool may be positioned in the second apertures 8 and 18 so that the tool may extend horizontally from the first aperture 18 of the second wall 15 to the first aperture 8 of the first wall 5. It should be understood that the first and second walls permit one or more tools to be held within the cavity of the device defined by the cavity 21 of the lid and the cavity 22 of the base 4 when the lid 3 is closed.

A light 27 that is able to emit ultraviolet light is attached to the lid. A power cord 28 is electronically coupled to the light 27 so that when the plug of the power cord 28 is plugged into an outlet electricity is transmitted to the light so that the light can emit ultraviolet light. The light may be actuated manually via a button or other actuation mechanism. Additionally, or as an alternative, the light may be actuated upon a detection that the lid is closed. For instance, a mechanical actuator such as a switch may be biased to an off position and may be moved to an on position when the lid is closed. A projection or finger of the lid may fit within an aperture or hole in the base to press on the switch to move it from the off position to the on position when the lid 3 is in the closed position. A switch may also be connected to the power cord 28 to turn on or off the light 27 as well.

The light 27 may be powered for a predetermined period of time after the lid 3 is closed. For example, the device 1 may be configured so that when the lid 3 is closed, the switch for activating the light 27 is moved to an on position for only a predetermined period of time. The predetermined period of time depends on the wattage of the ultraviolet light being applied. Preferably, the wattage of the light is such that the predetermined period of time needed to disinfect the surface of a tool exposed to the light is between five seconds and one minute, such as a ten second, twenty second, or thirty second time period. In other embodiments, the light may always be on when the lid is closed. The light that is emitted may be configured so that disinfection of tools may be provided via the emitted light without affecting metallurgical properties of the tools.

The device 1 may also include a timer that provides an audible warning to indicate when the predetermined time period has ended. A display unit along with one or more buttons may also be attached to the lid or the base to provide a visual indication of the status of the disinfection process (e.g. a timer indicating how much time is left before the tools positioned in the device 1 are disinfected, etc.). The display may also provide a visual warning when the timer indicates that the predetermined period of time has elapsed and the tools positioned within the device 1 are determined to be disinfected.

In some embodiments, the device 1 may include a detection mechanism to detect whether tools have been positioned within the device or not. The light may not be activated unless at least one tool is detected as being within the device 1. The detection mechanism may be a weight based mechanism or may be another type of sensor such as a proximity sensor or other type of detector. In some embodiments of my device, the first and second walls 5 and 15 may not be present. For those embodiments, the first and second end walls 11 and 12 may have one or more recesses formed therein for receiving and holding portions of one or more tools within the cavity 22 of the base 4 of the device 1. In yet other embodiments, such recesses or apertures in the end walls may be present along with one or more of the first and second walls 5, 15.

Figure 2:
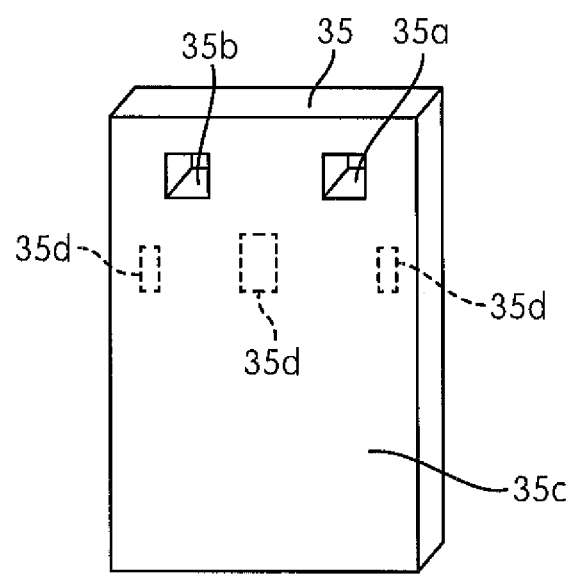
FIG. 2 is a fragmentary view of an exemplary embodiment of a wall that may be positioned in the cavity of the device or that may be used as an end wall of the base of the device that helps define the cavity of the device.

An example of an end wall construction that may be utilized in embodiments of my device is shown in FIG. 2. The end wall 35 includes apertures 35b and 35a. The apertures may be holes or may be recesses formed in only a portion of the wall so that the outer surface of the end wall 35 still forms a full enclosure for the cavity 22 of the base. The inner surface 35c of the end wall may face into the cavity 22 and help define the cavity 22. The apertures 35a and 35b may be recesses formed in the end wall 35 such that the inner surface 35 has depressions formed therein. The apertures 35a and 35b are preferably horizontally spaced apart from each other for receiving an end portion of a tool that may be positioned in the device. In other embodiments, there may be multiple rows of horizontally spaced apart apertures. Each row may be vertically spaced from another row and the horizontal spacing of the apertures may be configured so that the apertures of a lower row are offset relative to the row above the lower row. An example of the offset lower row of apertures is shown in broken line in FIG. 2.

In yet other embodiments, one or more removable racks may be positionable within the cavity 22 so that tools may be placed on the one or more racks and the racks may subsequently be positioned within the cavity 22 for positioning the tools within the cavity for disinfecting the tools. Each of the racks may have legs to help support the racks within the cavity 22 of the base 4 or may have edge portions configured to interlock with or engage profiles or grooves within the base to position the rack within the cavity 22. It should be understood that the one or more racks may permit a user may take tools out of the cavity 22 after the tools were disinfected by touching the racks and without directly touching the tools.

The device 1 may also include a reflective liner. The liner may be positioned on the inner surface of the base and the inner surface of the lid to reflect the emitted ultraviolet light from the light 27. For example, the liner may be attached to the inner surface of the bottom, ends, and sides of the base and the inner surface of the top, ends and sides of the lid. The liner may also be attached to the first and second walls 5, 15 and the inner surface of the end walls 11, 12. The reflective liner can help reflect the emitted ultraviolet light back onto the tools held therein to increase the efficiency of the device and reduce the time needed for disinfecting the tools.

Figure 3:
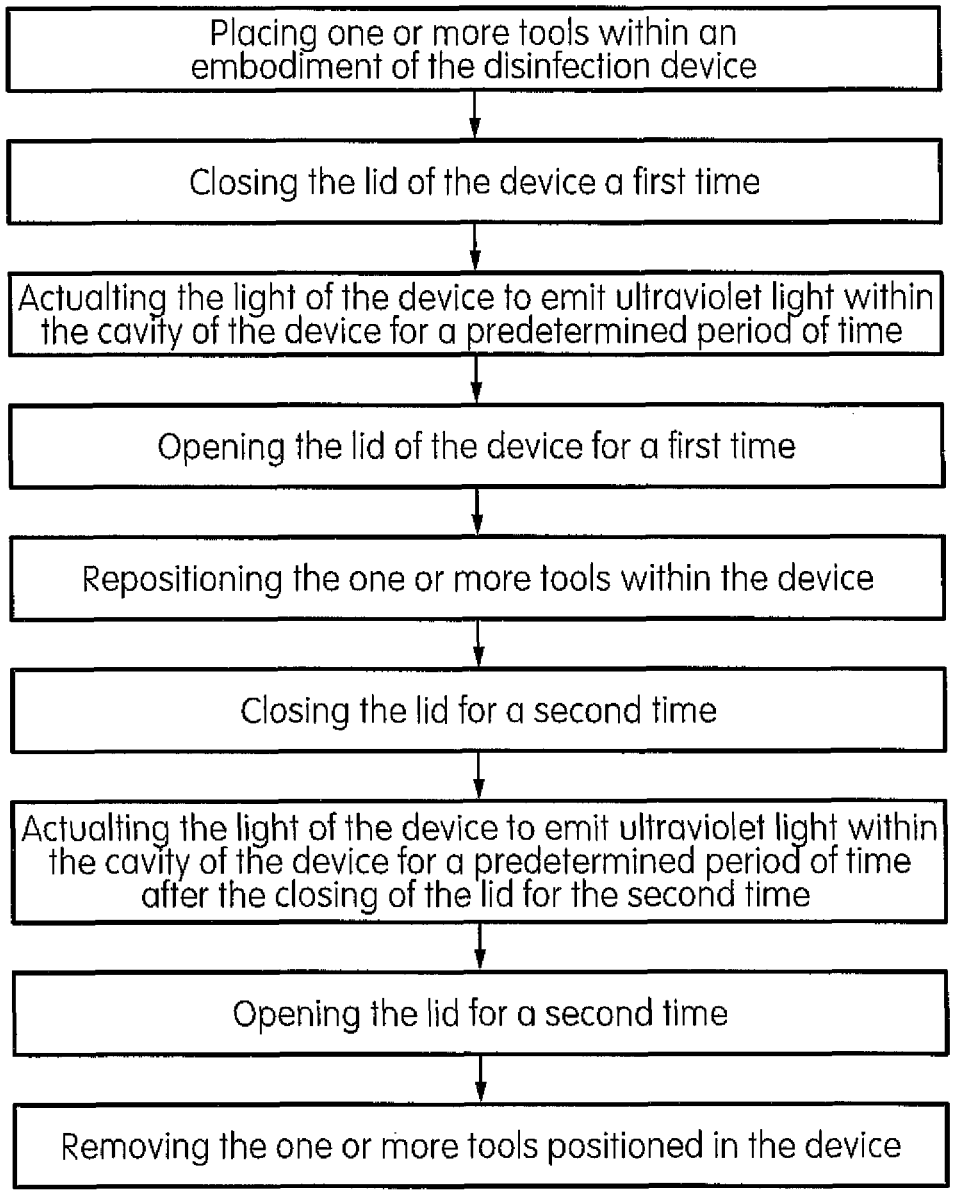
FIG. 3 is a flow chart illustrating an embodiment of a method of disinfecting tools such as medical tools or dental tools.

A method of using my device is shown in FIG. 3. The method includes the step of placing one or more tools within the cavity of the base. For instance, the tools may be positioned within aligned apertures of the first and second walls 5, 15 so that the walls hold the tools within the device when the lid 3 is closed. After the tools are positioned on the walls, the lid is closed and the light is subsequently actuated for at least a predetermined period of time to emit ultraviolet light to disinfect the tools. After the predetermined time period elapses, the lid is opened. The tools may then be repositioned so that the surfaces of the tools that may have been covered by a portion of the first and second walls 5, 15 or recesses of the end walls 11, 12 are now positioned to be exposed to the ultraviolet light emitted by the light 27 when the lid is closed. The lid may then be closed a second time and the light may be actuated a second time for the predetermined period of time to ensure the tools are fully disinfected. Thereafter, the lid may be opened and the tools may be removed. It should be understood that the tools can be repositioned, the lid closed a third time, and the light applied a third time prior to a third opening of the lid and a removal of the tools as well. In yet other embodiments of the method, the tools may be repositioned even more times similarly to the repositioning and reapplication of light as noted above.

Figure 4A:
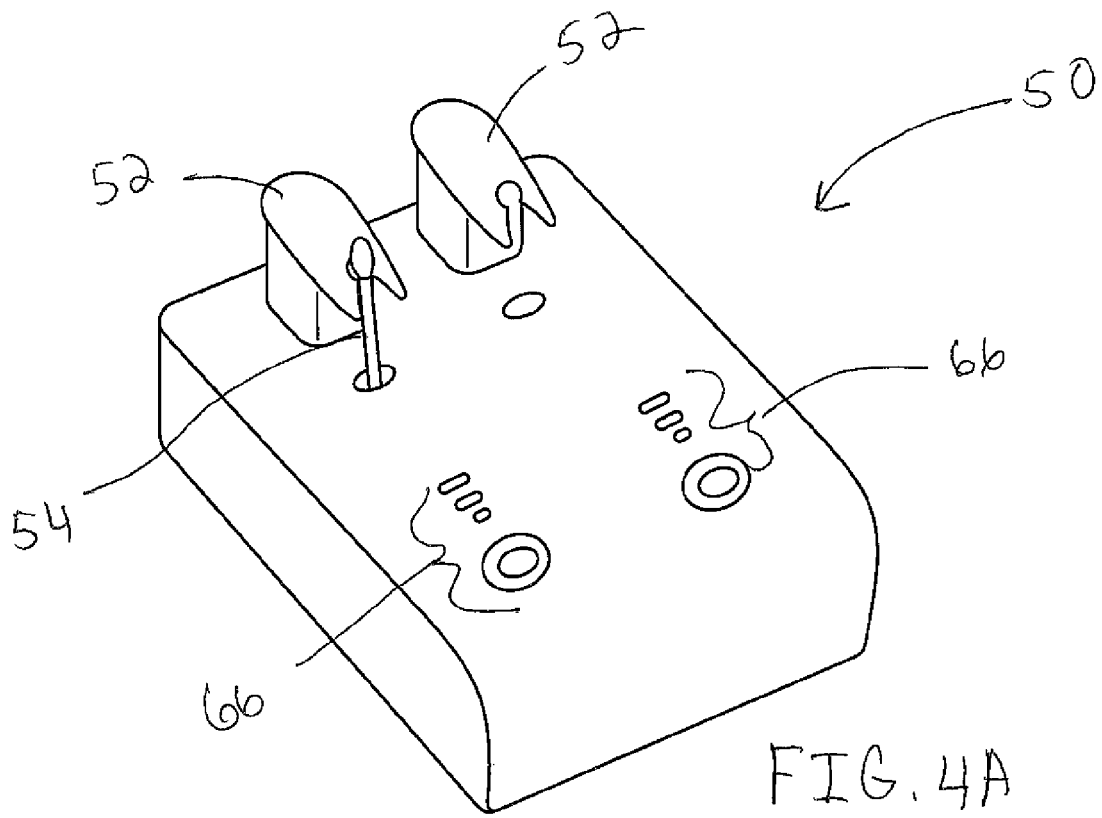
FIG. 4A is a perspective view of yet another exemplary embodiment of the present invention.
Figure 4B:
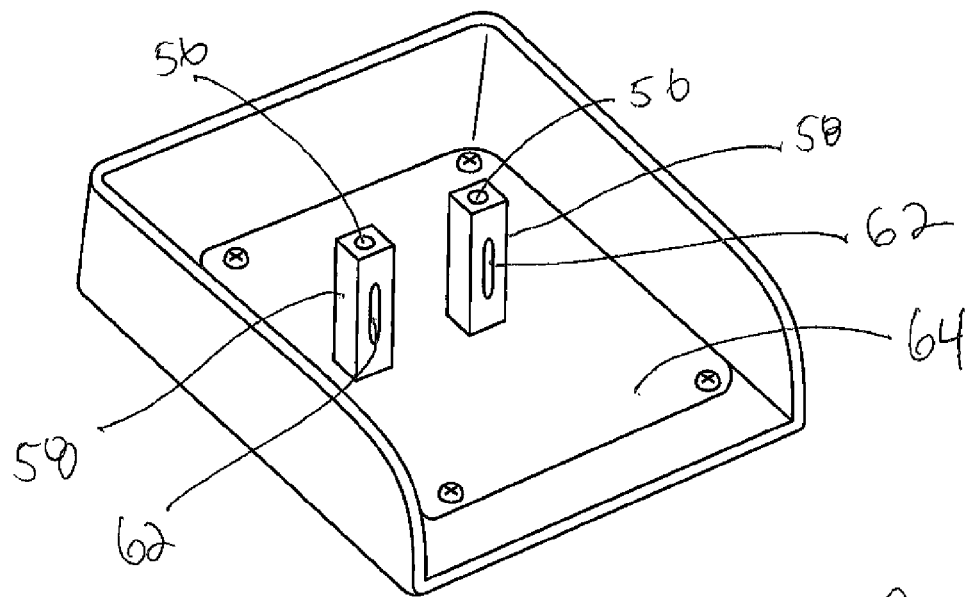
FIG. 4B is a perspective view of the exemplary embodiment shown in FIG. 4A without the cover portion.

FIG. 4A-4B includes ultraviolet disinfection within an obturator oven 50. The oven 50 may include at least one holder (e.g., gripper, actuator member, actuator arm, and/or otherwise) 52 for receiving and holding a material (e.g., a dental instrument, such as an obturator, having gutta percha, the like and/or otherwise material) 54 above an opening 56 of a heating compartment 58 for movement (e.g., actuating movement) for use therein. The heating compartment 58 may include a generally elongated cavity (not shown) for receiving at least a portion of the material. In one specific embodiment, a heating element (not shown) and/or a disinfection device 62 may be provided about the cavity of the heating compartment for softening and/or killing microorganisms, respectively, on at least a portion of the material. Desirably, when the holder 52 is pushed down from a first position to a second position (wherein at least a portion of the obturator 54 enters the heater compartment 58) the heating element and/or light source (e.g., ultraviolet light) are activated (e.g., turned on). It is appreciated that operation of the actuating arm, the activation of the heating element and/or light source, and or other (e.g., timers, sensors, the like and/or otherwise) may be accomplished by a power source (internal such as battery or external via a plug) through a PCB (Printed Circuit Board) 64, a controller, a CPU an interface 66 for selecting temperature, material type, heating and/or disinfecting/sterilizing time, and/or otherwise and combinations thereof.

While certain present preferred embodiments of the disinfection device, and methods of making and using the same have been shown and described above, it is to be distinctly understood that the invention is not limited thereto but may be otherwise variously embodied and practiced as may be understood by those of at least ordinary skill in the art. For example, the lid may be any of a number of shapes or profiles and the base could be any of a number of shapes and profiles. As another example, the wattage of the ultraviolet light or the number of ultraviolet emitting lights used in an embodiment of the device may be any of a number of different options (e.g. multiple lights of 30-60 W or one light of 100 W etc.). As another example, the first and second walls 5, 15 may be replaced with projections that extend from a floor of the base to hold one or more tools or holders positioned within the cavity of the base. Of course, many other variations could also be made as those of at least ordinary skill in the art may appreciate.

The invention claimed is:

1. A heating apparatus for heating and sterilizing or disinfecting a dental material used in dental treatment, the heating apparatus comprising:
   a heating compartment with a heating element for heating all or part of the dental material within the heating compartment;
   at least one holder for receiving and holding at least a part of the dental material used in dental treatment inside the heating compartment; and
   a disinfection device having a light source for sterilizing all or part of the dental material within the heating compartment;
   wherein the at least one holder is an actuating member;
   wherein the actuating member includes at least a first position and a second position such that in the first position the heating element, the light source, or both are turned off and in the second position, the heating element, the light source, or both are turned on;
   wherein a portion of the actuating member extends into the heating compartment such that a greater portion of the dental material is positioned within the heating compartment in the second position relative to the first position.

2. The heating apparatus of claim 1, wherein the light source emits ultra violet light.

3. The heating apparatus of claim 1, wherein the actuating member includes an actuator, triggered by detection of the actuating member being in the second position, to enable both the heat to be output from the heating element and light to be output from the light source.

4. The heating apparatus of claim 1, further comprising a light compartment seal to block light output from the light source from exiting the heating compartment, wherein the dental material and/or the actuating member forms part of the light compartment seal.

5. The heating apparatus of claim 4, wherein the dental material and/or the actuating member forms part of the light compartment seal when the actuating member is in the second position.

6. The heating apparatus of claim 4, further comprising a controller to control heat output and the light output so that the heat output and the light output may be pulsed at the same time or at different time.

7. The heating apparatus of claim 1, wherein the heating compartment is disposed within a housing having an exterior to surface, the heating compartment including an internal cavity that extends therein to an opening, which extends through the exterior top surface of the housing.

8. The heating apparatus of claim 1, further comprising a rechargeable battery unit for powering the heating element.

* * * * *